United States Patent [19]

Brandley et al.

[11] Patent Number: 5,428,025
[45] Date of Patent: Jun. 27, 1995

[54] METHOD OF TREATING INFLAMMATION BY BLOCKING ELAM-1 RECEPTOR SITES

[75] Inventors: Brian K. Brandley, Alameda; Michael Tiemeyer; Stuart J. Swiedler, both of Oakland; Margaret Moreland, Berkeley; Hans Schweingruber, Mountain View, all of Calif.

[73] Assignee: Glycomed Incorporated, Alameda, Calif.

[21] Appl. No.: 844,101

[22] Filed: Mar. 2, 1992

Related U.S. Application Data

[62] Division of Ser. No. 559,856, Jul. 30, 1990, Pat. No. 5,211,936.

[51] Int. Cl.⁶ .................... A01N 43/04; A61K 31/73
[52] U.S. Cl. ........................................ 514/55; 514/61
[58] Field of Search .................... 514/8, 55.61

[56] References Cited

U.S. PATENT DOCUMENTS

4,330,299  5/1982  Cerami .

FOREIGN PATENT DOCUMENTS

0319253   6/1989   European Pat. Off. .
WO90/1330  11/1990  WIPO .
WO9119501  12/1991  WIPO .
WO9119502  12/1991  WIPO .

OTHER PUBLICATIONS

Brandley and Schnarr, *J. Leuk. Biol.*, 40:97–111 (1986).
Sharon and Lis, *Science*, 246:227–246, (1989).
Dodd and Jessel, *J. Neurosci.*, 5:3278–3294 (1985).
Regan et al., *Proc. Natl. Acad. Sci. USA*, 83:2248–2252 (1986).
Constantine–Paton et al., *Nature*, 324:459–462 (1986).
Tiemeyer et al., *J. Biol. Chem.*, 263:1671–1681 (1989).
Bevilacqua et al., *Proc. Natl. Acad. Sci. USA*, 84:9238–9242 (1987).
Fukuda et al., *J. Biol. Chem.*, 261:2376–2383 (1986).
Magnani et al., *J. Biol. Chem.*, 257:14365–14369 (1982).
Hakomori et al., *Biochem. Biophys. Res. Comm.*, 113:791–798 (1983).
Fukushi et al., *J. Exp. Med.*, 160:506–520 (1984).
Geng et al., *Nature*, 343:757–760 (1990).
Johnston et al., *Cell*, 56:1033–1044 (1989).
Geoffroy and Rosen, *J. Cell Biol.*, 109:2463–2469 (1989).
Lasky et al., *Cell*, 56:1045–1055 (1989).
Bevilacqua et al., *Science*, 243:1160–1165 (1989).
European Search Report.
Lamblin et al., *Journal of Biological Chemistry* (1984) 259(14):9051–9058.
Stanley et al., *Journal of Biological Chemistry* (1988) 263(23):11374–11381.

*Primary Examiner*—Jill Warden
*Assistant Examiner*—Sheela J. Huff
*Attorney, Agent, or Firm*—Gregory J. Giotta; Karl Bozicevic; Valeta Gregg-Emery

[57] ABSTRACT

Ligands in the form of N-acetyllactosamines which bind to endothelial leukocyte adhesion molecule-1 (ELAM-1) are disclosed. The ligand compounds can be formulated into pharmaceutical compositions and/or assay compositions used to alleviate inflammation and assay for the presence of (qualitative) and amount of (quantitative) ELAM-1 and thereby determine the presence, location and degree of inflammation. The ligands are encompassed by general structural formula I as follows:

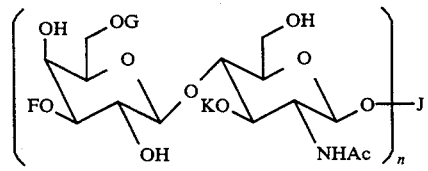

wherein one of F and G is hydrogen and one is an N-acetyl neuraminic acid residue on the terminal unit and are both hydrogen on any other unit; J is hydrogen, a lactosylceramide or a linking group and K is hydrogen or a fucose residue and n is an integer of from 1 to 10 (preferably 3 or 4) with the proviso that n and K are defined such that at least one K is a fucose residue.

6 Claims, 2 Drawing Sheets

METHOD OF TREATING INFLAMMATION BY BLOCKING ELAM-1 RECEPTOR SITES

CROSS REFERENCE

This application is a divisional application of our earlier filed application Ser. No. 07/559,856, filed Jul. 30, 1990, U.S. Pat. No. 5,211,936, to which application we claim priority under 35 USC S120 and which application is incorporated herein by reference in its entirety.

FIELD OF THE INVENTION

This invention relates generally to determining the presence of and relieving the effects of inflammation. More specifically, this invention relates to carbohydrate ligands which bind to endothelial leukocyte adhesion molecule-1 (hereinafter ELAM-1) and to compositions containing such ligands which are useful in (a) determining the presence of ELAM-1, (b) assaying for areas of inflammation, and (c) relieving inflammation by blocking the effects of ELAM-1.

BACKGROUND OF THE INVENTION

While protein-protein interactions in cell recognition have been recognized for some time, only recently has the role of carbohydrates in physiologically relevant recognition been widely considered (See Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated with relatively few gene products, suggesting a plausible mechanism for establishing the information necessary to direct a wide range of cell-cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton, M., et al., *J. Biol. Chem.* (1986) 324:459; and Tiemeyer, M., et al., *J. Biol. Chem.* (1989) 3, 1671). Further, the question has been raised as to what is the leukocyte receptor for ELAM-1 (See Bevilacqua et al. Proc Natl. Acad. Sci. *USA* (1987) 84:9238).

Glycolipids have been identified in fetal tissue and a variety of human cancers, including CML cells (Fukuda, M. N., et al., *J. Biol. Chem.* (1986) 261:2376;Magnani, J. L., et al., *J. Biol. Chem.* (1982) 257:14365; Hakomori, S., et al., *Biochem. Biophys. Res. Comm.* (1983) 113:791), and are designated as sialyl-Le$^x$ structures. This has led to the hypothesis that these structures may be important in many developmental and oncogenic processes (J. L. Magnani et al., J. Biol. Chem. (1982) 257:14365). Smaller quantities of most of these carbohydrates can be found in normal human tissue (see Fukushi, Y., et al., *J. Exp. Med.* (1984) 160:506), but until now no function for these structures has been reported.

Adhesion of circulating neutrophils to stimulated vascular endothelium is a primary event of the inflammatory response. Several receptors have been implicated in this interaction, including a family of putative lectins that includes gp90$^{MEL}$ (Leu8), GMP-140 (PADGEM) and ELAM-1 (Gong, J.-G., et al., *Nature* (1990) 343:757; Johnston, G. I., et al., *Cell* (1989) 56:1033; Geoffroy, J. S., and Rosen, S. D., *J. Cell Biol.* (1989) 109:2463; Lasky, L. A., et al., *Cell* (1989) 56:1045). While these receptors each contain a domain with sequence homology to calcium dependent lectins, only gp90$^{MEL}$ has been demonstrated to recognize a carbohydrate (See J. S. Geoffrey et al., *J Cell Biol.* (1989) 109:2463). Endogenous ligands for these receptors have yet to be identified.

ELAM-1 is particularly interesting because of its transient expression on endothelial cells in response to IL-1 or TNF (Bevilacqua, M. P., et al., *Science* (1989) 243:1160). The time course of this induced expression (2-8 h) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding for the ELAM-1 receptor. The present inventors have now found that ELAM-1 recognizes a carbohydrate present on a subset of structurally related acidic glycolipids isolated from human leukocytes and developed the present invention.

SUMMARY OF THE INVENTION

Ligand molecules capable of binding to and interrupting the biological chain of events associated with ELAM-1 are disclosed. The ligands are in the form of N-acetyllactosamines which can be labeled and/or formulated to provide: (1) compositions useful in assaying a sample for the presence of ELAM-1, (2) compositions useful in detecting the cite of inflammation in a patient, and (3) pharmaceutical composition useful in treating acute inflammation.

A primary object of the invention is to provide an ELAM-1 ligand in a useful formulation.

Another object is to provide a composition comprising an ELAM-1 ligand which can be used to assay for the presence of ELAM-1 in a sample.

Another object is to provide a pharmaceutical formulation containing an ELAM-1 ligand which is useful in treating inflammation.

Other objects include providing methods to treat inflammation and to determine the cite of inflammation.

An advantage of the invention is that the ligands are in the form of non-toxic N-acetyllactosamines which effectively bind ELAM-1 and thereby interrupt its role in acute inflammatory reactions.

A feature of the present invention is that the ligand can be labeled and the labeled ligand administered to determine a cite of inflammation.

These and other objects, advantages and features of the present invention will become apparent to those persons skilled in the art upon reading the details of the isolation, structure, formulation and usage as more fully set forth below, references being made to the accompanying FIGURES and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF PREFERRED EMBODIMENTS

Figure 1:
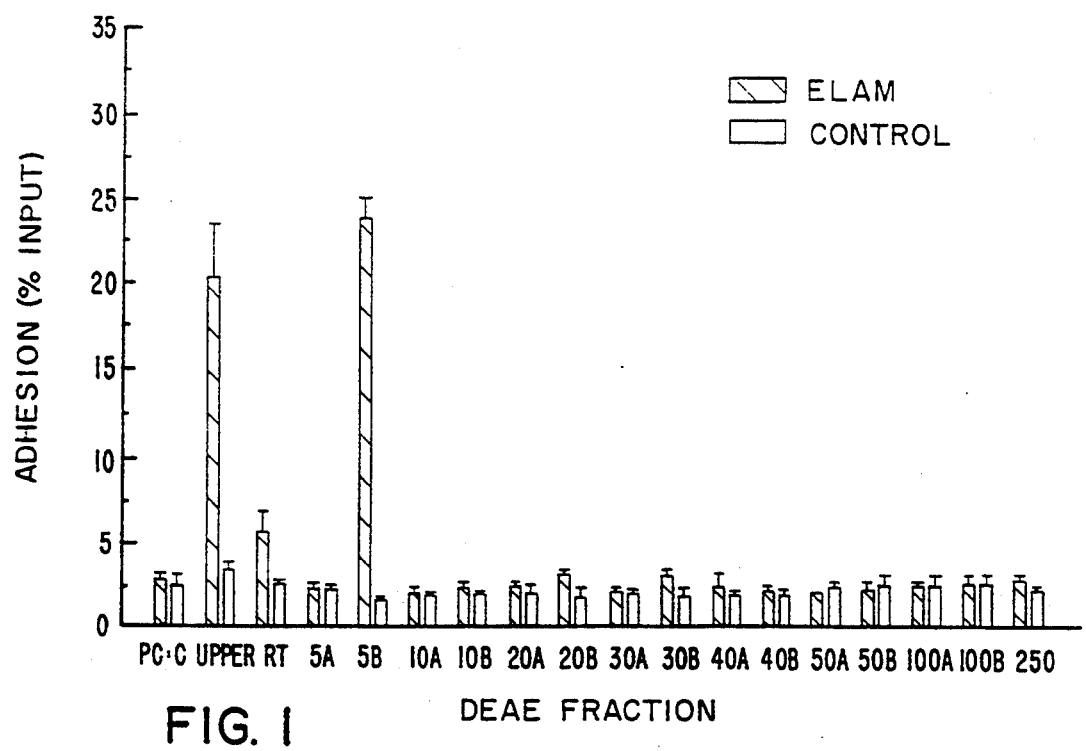
FIG. 1 is a graph showing the results of tests carried out to determine the adhesion of ELAM-transfected COS cells to neutrophil glycolipids which were separated by charge.
Figure 2:
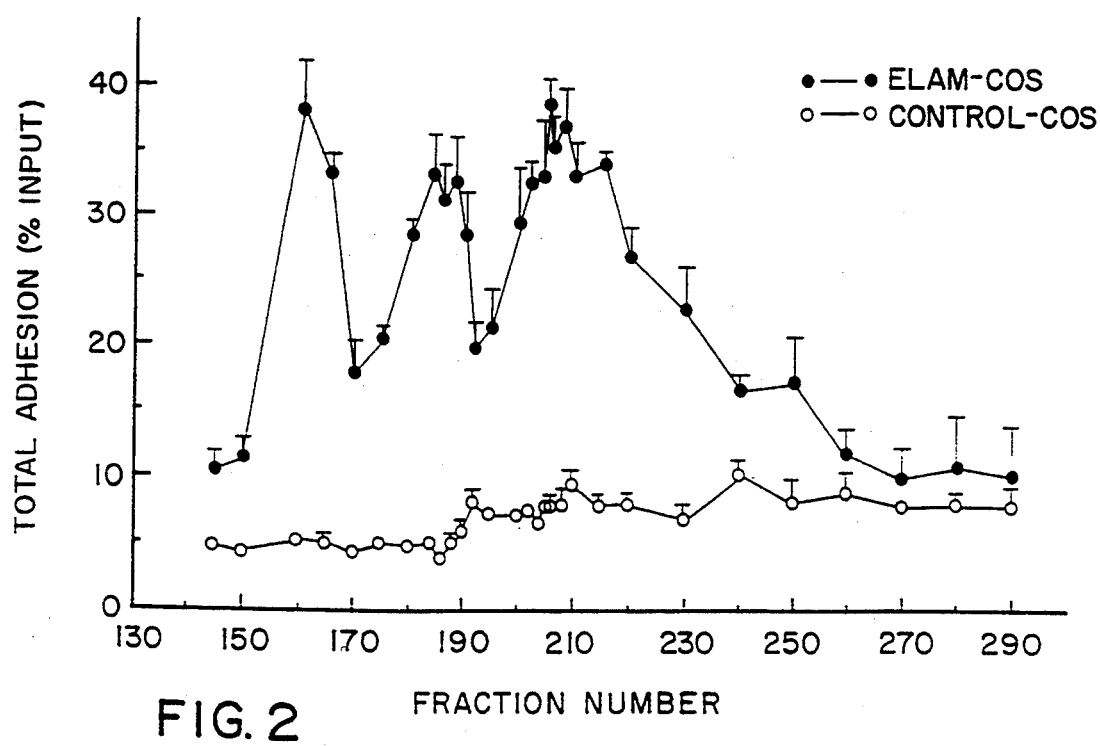
FIG. 2 is a graph comparing the percent adhesion of ELAM-transfected COS cells with the percent adhesion of control COS cells.
Figure 3:
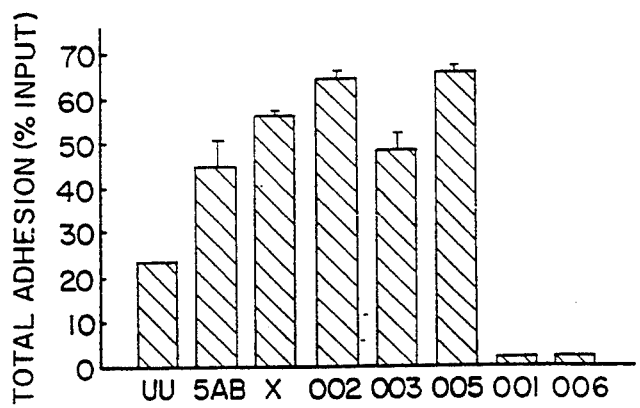
FIG. 3 graphically shows the effect of glycolipid purification on the adhesion of the glycolipids to ELAM-transfected COS cells.

Before the present ELAM-1 ligands and composition containing such ligands and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a" "an" and "the" include plural referents unless the context clearly dictates otherwise. Thus, for example, reference to "a glycolipid" includes mixtures of glycolipids, reference to "an ELAM-1 ligand" includes reference to mixtures of such ligand, reference to "the method" includes one or more methods and/or steps of the type described herein and/or which will become apparent to those persons skilled in the art upon reading this disclosure and so forth.

A. General Overview

It is known that for an acute inflammatory response to occur, circulating neutrophils must bind to and penetrate the vascular wall and access the site of injury. Several receptors have been implicated in this interaction, including a family of putative carbohydrate receptors. One receptor which has not been previously isolated or identified is the endogenous carbohydrate ligands for endothelial leukocyte adhesion molecule-1 (hereinafter ELAM-1).

Radiolabeled COS cells expressing cell surface ELAM-1 were used as probes to screen human leukocyte derived glycolipids. ELAM-1 transfected COS cells adhered to a subset of sialylated glycolipids which were resolved on TLC plates or adsorbed on PVC microliter wells. Adhesion to these glycolipids required calcium, but was not inhibited by heparin, chondroitin sulfate, keratin sulfate, or yeast phosphomannan. Monosaccharide composition, linkage analysis and FAB mass spectrometry of the purified glycolipids indicated that the ligands for ELAM-1 share common structural characteristics, consisting of lactosyl ceramides with a variable number of N-acetyl lactosamine repeats, a terminal N-acetyl neuraminic acid and a fucose branch on at least one of the N-acetylglucosamine residues. The N-acetylneuraminic acid and fucose appear to be required for recognition and binding by ELAM-1.

One mechanism by which glycolipids could mediate intercellular events would involve the recognition of the glycolipid oligosaccharide moiety on one cell by a specific carbohydrate-binding protein (lectin) on an opposing cell. Data generated in connection with the present invention indicate that acidic glycolipids containing the sialyl-Le$^x$ determinant isolated from leukocytes and ELAM-1 function as such an oligosaccharide-lectin pair, participating in the interaction of neutrophils with the surface of cells of activated vascular endothelium. Many protein-protein interactions have been implicated in neutrophilendothelium transmigration (see Lo, S. K., et al., *J. Immunol.* (1989) 143:3325; Osborn, L., et al., *Cell* (1989) 59:1203; Larsen, F., et al., *Cell* (1989) 59:305; and Arnaout, M. A., *Blood* (1990) 75:1037). While not wishing to be bound to any theory, the present inventors believe it is likely that this lectin-carbohydrate interaction is only one step in a series that result in neutrophil extravasation.

The affinity of ELAM-1 for the glycolipids described here has been tested. Accordingly, these glycolipids are believed to be useful in mediating a specific, but possibly weak adhesion that is then stabilized and elaborated by the participation of other receptors. Oligosaccharides with the structure described herein, or modifications of these structures, are believed to be capable of blocking the interaction of neutrophils with activated vascular endothelium mediated by ELAM-1, and hence provide useful pharmaceutically active anti-inflammatory agents.

B. Recombinant Production of Putative ELAM-1 Ligands

A complete cDNA for the ELAM-1 receptor was obtained by PCR starting with total RNA isolated from IL-1 stimulated human umbilical vein endothelium. The resulting cDNA was inserted into the CDM8 plasmid (see Aruffo, A., and Seed, B., *Proc. Natl. Acad. Sci. USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua, M. P., et al., *Science,* (1989) 243:1160; Polte, T., et al., *Nucleic Acids Res.* (1990) 18:1083; Hession, C., et al., *Proc. Natl. Acad. Sci. USA* (1990) 87:1673). The complete nucleotide sequence of the ELAM-1 cDNA and predicted amino acid sequence of the ELAM-1 protein are given in the above cited article by Bevilacqua et al., which is incorporated herein by reference to disclose these sequences.

COS cells, expressing membrane-bound ELAM-1, were metabolically radiolabeled with $^{32}PO_4$ and used as probes in two assay systems to screen for recognition of glycolipids. In the first, glycolipids were adsorbed to the bottoms of PVC microliter wells, while in the second they were resolved on TLC plates. In both assays these glycolipids were probed for their ability to support adhesion of ELAM-transfected COS cells, untransfected COS cells, or COS cells transfected with a plasmid containing an irrelevant cDNA, under conditions of controlled detachment force (see Swank-Hill, P., et al., *Anal. Biochem.* (1987) 183:27; and Blackburn, C. C., et al., *J. Biol. Chem.* (1986) 261:2873 each of which is incorporated herein by reference to disclose the details of such assaying methodology).

The glycolipids used in these adhesion experiments were derived from leukocytes collected from patients with chronic myelogenous leukemia (CML) undergoing therapeutic leukophoresis. Denatured cellular material equivalent to about 500 ml of packed cells was extracted and partitioned by the method of Fredman and Svennerholm (Svennerholm, L., and Fredman, P., *Biochim. Biophys. Acta* (1980) 617.:97 which is incorporated herein by reference to disclose such methodology). Glycolipids partitioning into the upper phase were freed of phospholipids by saponification. Glycolipids from the saponified upper phase, containing approximately 100 $\mu$mol sialic acid, were initially screened for ELAM-mediated cell adhesion. Up to 25% of the ELAM-transfected COS cells adhered to the crude upper phase glycolipid mixture adsorbed to the bottom of PVC microliter wells. Cell adhesion directly to glycolipids resolved on TLC plates revealed specific recognition of several relatively polar bands that stained with resorcinol.

C. Separating and Isolating Putative Glycolipid ELAM-1 Receptors

Since the initial screening suggested that ELAM-1 recognized ligands may be acidic glycolipids, the total glycolipids were fractionated by charge on a DEAE-Sepharose (acetate form) column (Pharmacia, Fast Flow). The material in the column run-through and in fractions eluted by step-wise increases in salt concentration (from 5 mM to 250 mM potassium acetate in methanol) were screened for cell adhesion. Virtually all of the ELAM-1 binding activity was eluted with 5 mM potassium acetate, suggesting that the carbohydrate ligand was monosialylated (See the above cited and incorporated Svennerholm article for details of such a procedure). Cell adhesion to these glycolipids was completely blocked by the removal of calcium, but was not inhibited by a number of carbohydrates of known structure, including heparin, chondroitin sulfate, keratin sulfate, or yeast phosphomannan (at 100 $\mu$g/ml).

D. Testing Putative Receptors for ELAM-1 Affinity

The mixture of glycolipids eluting from the DEAE column in 5 mM KAc was subsequently fractionated by polarity on beaded silica columns (Iatrobead, Iatron Laboratories). Cell adhesion to aliquots of these fractions revealed three peaks of ELAM-1 binding activity that corresponded to the elution positions (as determined by TLC with resorcinol staining) of the previously identified sialylated glycolipids. Fractions from this column, pooled by their ability to support adhesion of ELAM-transfected COS cells, were separated into three active glycolipid bands by a second Iatrobead column. The more polar two of these were each resolved into two bands by preparative TLC in 55:35:20 (n-butanol:ethanol:water), to yield a total of three ELAM-1 recognized bands in addition to several inactive bands. The most prevalent of the active bands (Band 3) was approximately 0.03% of the total sialic acid found in the crude upper phase mixture, and supported adhesion of up to 60% of the input ELAM-transfected COS cells. These same glycolipid bands are present at much lower levels in HL-60 cell glycolipid extracts. Taken together, the present inventors deduced that these data demonstrate that ELAM-1 is a calcium dependent lectin that recognizes a small subset of structurally related acidic glycolipid present on cells of myelocytic lineage.

E. Ligand Structure

To characterize the structure of the ligands, monosaccharide composition of the purified glycolipids was performed by acid hydrolysis followed by anion exchange chromatography and quantitation with pulsed amperometric detection (PAD, Dionex Corp.). Linkages were assigned by methylation followed by hydrolysis, reduction, acetylation and gas chromatography with mass detection. FAB mass spectrometry was performed on. Data from composition and mass spectrometry on the ELAM recognized Band 2 are consistent with the following structural formula II(a) and II(b).

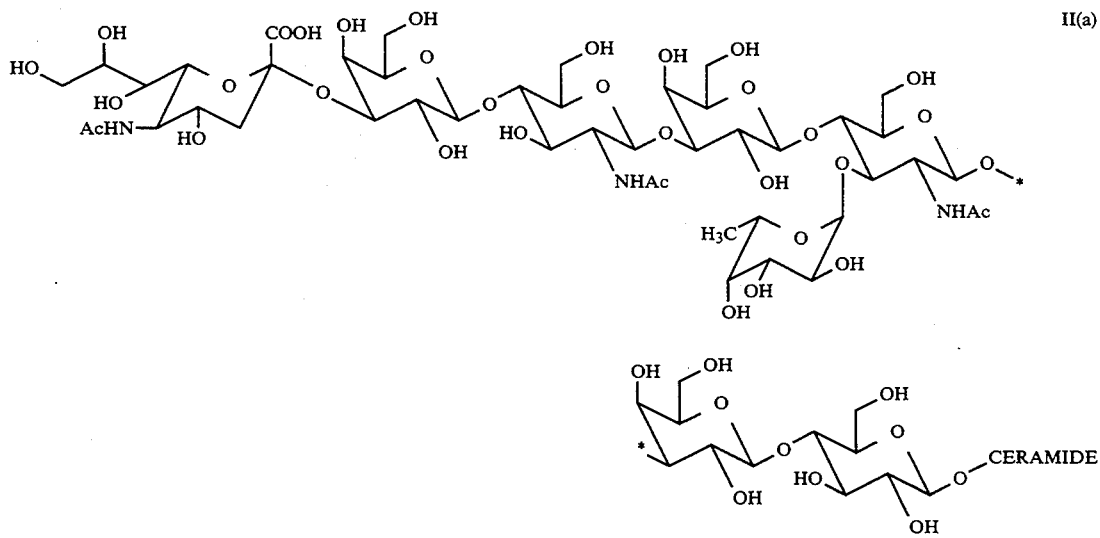

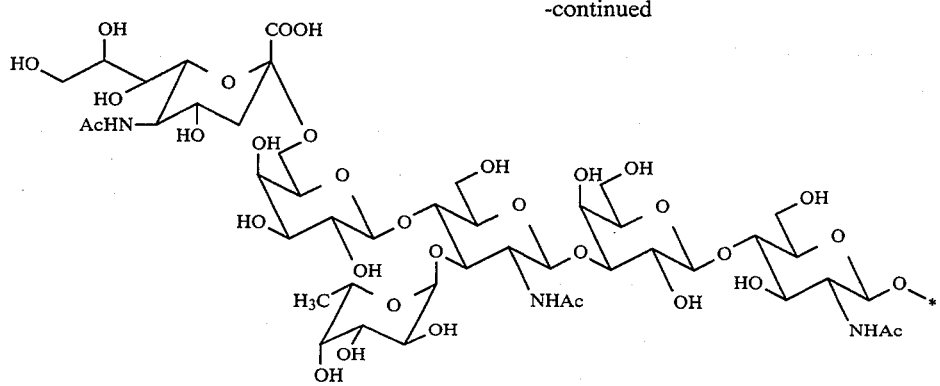

II(b)

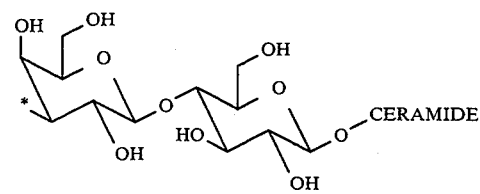

In formula II(a) and II(b) the Ac is acetyl and Ac is acetyl throughout this disclosure. Further, the fucose may be present on any of the lactosamine units and the ceramide is always optionally present it being a minor constituent of the particulars animal tissue from which the material was extracted.

Figure 4A:
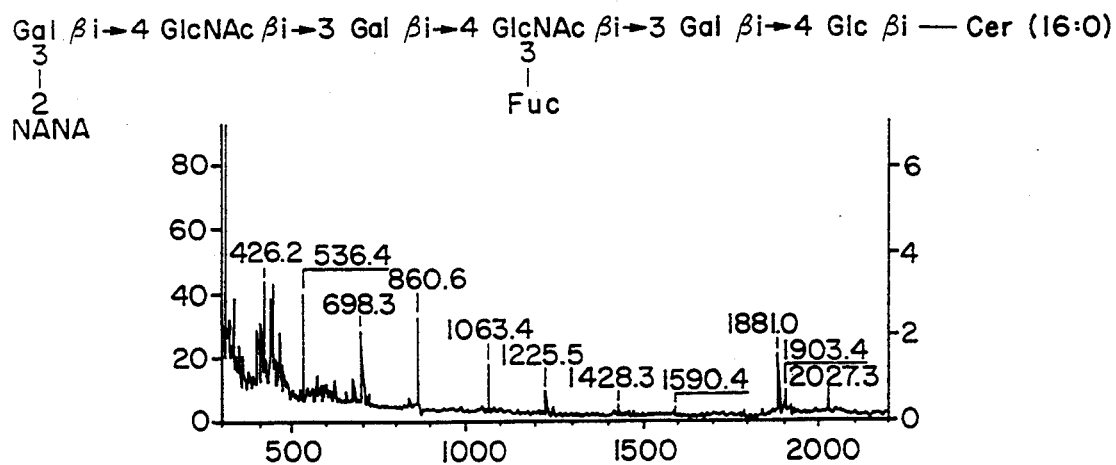
FIGS. 4A and 4B provide the basis for a comparison of a FAB mass spectrograph of a glycolipid recognized by ELAM-1 (4A) with a related glycolipid not recognized by ELAM-1 (4B).

The above structure is a lactosyl ceramide with two N-acetyl lactosamine repeating units, a terminal N-acetylneuraminic acid and a fucose on one of the N-acetylglucosamine residues. Composition data for this band indicated that there is one fucose for every two glucose residues, with two moles of N-acetylglucosamine, and 3 moles of galactose for each mole of glucose. Mass spectrometry (as shown in FIG. 4A) reveals a molecular ion at 2027 mass units, with major fragmentation products indicating a loss of a fucose, an N-acetylneuraminic acid, a hexose, an N-acetylhexosamine, hexose, deoxyhexose, N-acetylhexosamine, hexose, and hexose to the ceramide. Based on the mass spectrograph information and formulae II(a) and II(b) a subgeneric formula for the ELAM-1 ligand can be deduced to be the following:

fucose. Other repeating lactosamine units may be included. The "LINKER" is optional present and may be H or a lactosylceramide. In one embodiment of the invention the "LINKER" connects a plurality of the ligands to a support base. The support base is then contacted with a sample to assay for the presence of ELAM-1 in the sample.

Both the composition and the relative ratios of the mass ions at 2027 and 1881 suggest that this material is a mixture of two components, identical but for the presence of a fucose on 30-40% of the molecules. Data for the other active bands indicate that they are structurally related, varying in the number of the N-acetyl lactosamine repeating units, but each with a single N-acetyl neuraminic acid residue, and at least one fucose residue.

Figure 4B:
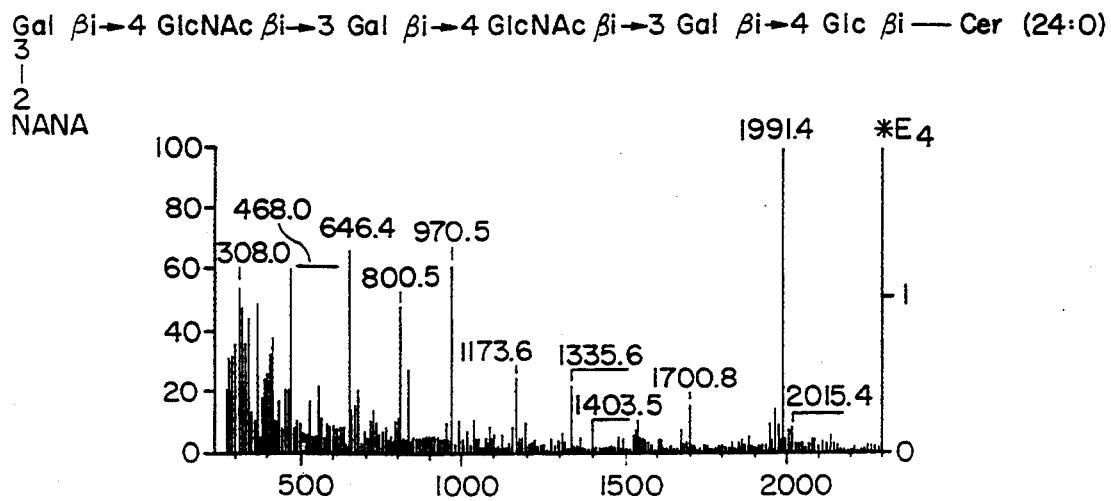

The structure of one of the nonbinding bands has been characterized (Band 1, FIG. 4B). This band contains an identical carbohydrate structure to band 2, but lacks the fucose residue. A second glycolipid that is not recognized by ELAM-1 also lacks fucose. Therefore, it appears that the fucose is essential for binding activity.

Linkage analysis on ELAM-recognized bands 3 and 5

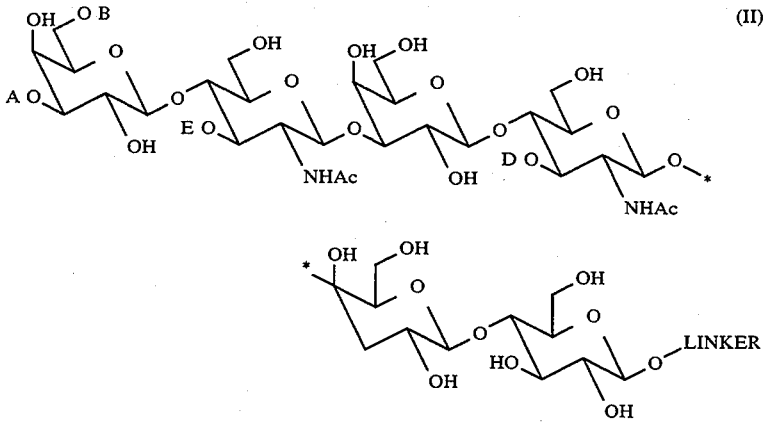

(II)

In formula II above, A and B are each different and one is H and one is an N-acetyl neuraminic acid residue. D and E are each independently hydrogen or a fucose residue with the proviso that at least one of D or E is reveal that the glucose residue is substituted at the 4 position, the galactose at the 3 position and the N-acetylglucosamine is a mixture of 4 substituted and 3,4 disubstituted residues. Treatment of the mixed glycolipids with mild acid under conditions that selectively cleave sialic acid and fucose (Dahms, N. M., and Schnaar, R. L., *J. Neurosci.* (1983) 3:806), eliminates ELAM-COS binding, confirming the requirement for these sugars. Taken together, these data indicate that the ligands for ELAM-1 are glycolipid consisting of lactosyl ceramide and N-acetyl lactosamine repeats, with a terminal N-acetyl neuraminic acid residue and a fucose branch on one of the N-acetylglucosamine residues.

Based on the above information, specific formula II(a) and II(b) and subgeneric formula II, a generic formula I is proposed as a ligand capable of effectively binding to the protein ELAM-1. The ligand will include (a) one or more repeating units of N-acetyl lactosamine (b) an N-acetyl neuraminic acid residue which is (c) connected to an N-acetyl lactoramine via a 2–3 linkage (II(a)) or a 2–6 linkage (II(b)); and includes at least one fucose residue. Accordingly, a generic structure for the ligands of the present invention is general structural formula I as follows:

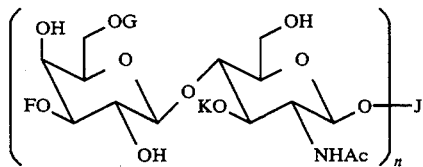

wherein one of F and G is hydrogen and one is an N-acetyl neuraminic acid residue on the terminal unit and are both hydrogen on any other unit; J is hydrogen, a lactosylceramide or a linking group; and K is hydrogen or a fucose residue and n is an integer of from 1 to 10 with the proviso that n and K are defined such that at least one K is a fucose residue (n is preferably 3 or 4).

EXAMPLES

The following examples are provided so as to provide those of ordinary skill in the art with a complete disclosure and description of how to make the compounds and compositions of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

EXAMPLE 1

Recombinant Production of Putative ELAM-1 Ligands

Upper phase, saponified neutrophil glycolipids (100 μmol sialic acid) were loaded on a 200 ml DEAE-Sepharose Fast Flow column (Pharmacia) in 4:8:3 (chloroform:methanol:water) washed with three column volumes of methanol, and eluted with 200 ml steps of 5, 10, 20, 50, 100 and 250 mM potassium acetate in methanol (For further details see Blackburn et al., *J. Biol. Chem.* (1986) 261:2873 which is incorporated herein by reference to describe and disclose such a procedure). Fractions were desalted and aliquots then dried, resuspended in 100% ethanol containing 1 μM phosphatidyl choline and 4 μM cholesterol, and an equal volume of water added. This material was added to PVC microliter wells (50 μl/well) and the glycolipids adsorbed for 80 min at room temperature (For details on this procedure see Aruffo, *Proc. Natl. Acad. Sci. USA*, (1987) 84:8573). A full length cDNA encoding ELAM-1 was obtained by 35 cycles of the polymerase chain reaction with 1 μg of total RNA extracted from IL-1 stimulated human umbilical vein endothelial cells, utilizing primers complementary to the untranslated flanking sequences (5'-GGTGCGGCCGCGGCCAGAGACCCGAG-GAGAG-3' and 5'-GGTGTCGACCCCACCT-GAGAGATCCTGTG-3'). The 2Kb insert generated was gel purified, directionally cloned into the mammalian expression vector, CDM8 that had been modified by the insertion of a SalI site into the polylinker, and grown in *E. coli* (MC1061/p3). Plasmids were isolated from individual colonies and used to transfect COS cells. Putative ELAM-1 encoding plasmids were selected based on the ability of these transfected COS cells to support HL-60 cell adhesion 72 h posttransfection.

A positive cDNA whose sequence corresponded to the published sequence of ELAM-1 with two nucleic acid substitutions was used in all experiments. COS cells were transfected with 1 μg of this plasmid DNA per $3.5-5.0 \times 10^5$ cells, with 400 μg/ml DEAE-dextran and 100 μM chloroquine for 4 h, followed by a brief exposure to 10% DMSO in PBS. Cells were metabolically radiolabeled overnight with carrier free $^{32}PO_4$ and harvested in PBS supplemented with 0.02% azide and 2 mM EDTA at 72 h post-transfection for use in cell adhesion studies. The adsorbed lipids were screened for their ability to support adhesion of ELAM-transfected COS cells using a centrifugation assay (described in detail in the above cited Blackburn article). The results demonstrate that the majority of the adhesion-supporting material in the unfractionated neutrophil glycolipids elutes with the 5 mM salt fractions, suggesting a monosialylated glycolipid. The pooled material eluted with 5 mM salt was used in further purification procedures.

EXAMPLE 2

Determining Putative Glycolipid ELAM-1 Receptors

The desalted material eluted from DEAE with 5 mM salt (approximately 11.5 μmols sialic acid) was loaded onto a 100 ml beaded silica column (Iatrobeads, 100 μm bead dia.) in 60:35:8 (chloroform:methanol:water) and eluted isocratically with a gravity feed of the same solvent. Fractions (2.5 ml) were collected, dried and screened for adhesion of ELAM-transfected COS cells by the PVC microliter well adsorption assay described above in Example 1 (panel A), or by a TLC overlay procedure (panel C, 373). Fractions from the Iatrobead column were pooled based on their ability to support adhesion of ELAM-transfected COS cells in the microliter assay. These pools were run on High Performance Silica TLC (HPTLC) plates in 60:35:10 (chloroform:methanol:0.25% aqueous KCl). Panel B shows a resorcinol stain of such a plate. Companion plates were coated with polyisobutyl methacrylate (0.005% in hexane) and probed with ELAM transfected COS or control COS (metabolically radiolabeled with $^{32}PO_4$) using conditions of controlled detachment force as described in detail in Swank-Hill et al. *Anal. Biochem* (1987) 163:27 which is incorporated herein by reference. Autoradiographs of a TLC plate probed with ELAM-transfected COS cells was made. The bands of the autoradiographs were compared with control-COS probed autoradiographs. The pools containing the bands recognized specifically by the ELAM-transfected COS cells were taken through further purification.

EXAMPLE 3

Glycolipids at each step of purification were adsorbed to PVC microliter wells and probed with ELAM transfected or control COS cells as described in Example 1. Results from a single input glycolipid concentration were shown to demonstrate increased specific binding activity achieved with purification of the glycolipid.

Use and Administration

The compounds of the invention such as various ligands of structural formula I can be administered to a subject either prophylactically or after inflammation. The ligands are administered with a pharmaceutically acceptable carrier, the nature of the carrier differing with the mode of administration, for example, oral administration, usually using a solid carrier and I.V. administration a liquid salt solution carrier. The method of choice, can be accomplished using a variety of excipients including, for example, pharmaceutical grades of mannitol, lactose, starch, magnesium, stearate, sodium saccharin cellulose, magnesium carbonate, and the like. These oral compositions may be taken in the form of solutions, suspensions, tablets, pills, capsules, sustained release formulations, or powders. Particularly useful is the administration of the subject ligand molecules directly in transdermal formulations with permeation enhancers such as DMSO.

A sufficient amount of ligand molecules should be administered to bind to a substantial portion of the ELAM-1 expected to cause or actually causing inflammation so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The ligand molecules of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The ligands in the form of glycolipids and carbohydrates or more specifically compounds of formula II(a) or II(b) can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art see, e.g., Remington's Pharmaceutical Sciences, Mack Publishing Company, Easton, Pa., 17th edition, 1985. The composition or formulation to be administered will, in any event, contain a quantity of the ligand molecules adequate to achieve the desired state in the subject being treated.

The various ligand compounds of the present invention can be used by themselves or in combination with pharmaceutically acceptable excipient materials as described above. However, the ligand compounds of the invention can be made as conjugates wherein the compounds of the invention are linked in some manner to a label. By forming such conjugates, the ligand compounds of the invention act as biochemical delivery systems for the label so that a cite of inflammation can be detected.

The ligand molecules of the invention could also be used as laboratory probes to test for the presence of ELAM-1 in a sample. Such probes are preferably labeled such as with a radioactive label.

The instant invention is shown and described herein in what is considered to be the most practical and preferred embodiments. It is recognized, however, that departures may be made therefrom which are within the scope of the invention, and that obvious modifications will occur to one skilled in the art upon reading this disclosure.

What is claimed is:

1. A method of treating inflammation, comprising:
   administering to a patient a therapeutically effective amount of a compound having the following general structural formula:

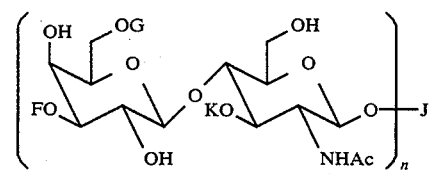

wherein one of F and G is hydrogen and one is an N-acetyl neuraminic acid residue on the terminal unit and are both hydrogen on any other unit; J is hydrogen or a linking group and K is hydrogen or a fucose residue and n is an integer of from 1 to 10 with the proviso that n and K are defined such that at least one K is a fucose residue.

2. The method as claimed in claim 1, wherein n is 1 and K is a fucose residue.

3. The method as claimed in claim 1, wherein J is hydrogen.

4. The method as claimed in claim 1, wherein J is a linking group.

5. The method as claimed in claim 1 wherein G is hydrogen and F is an N-acetylneuraminic acid.

6. The method as claimed in claim 1, wherein n is 1, K is fucose, J is hydrogen, G is hydrogen and F is N-acetylneuraminic acid.

* * * * *